(12) United States Patent
Feinberg

(10) Patent No.: US 7,945,304 B2
(45) Date of Patent: May 17, 2011

(54) ULTRASOUND WITHIN MRI SCANNERS FOR GUIDANCE OF MRI PULSE SEQUENCES

(76) Inventor: David A. Feinberg, Bodega Bay, CA (US)

(*) Notice: Subject to any disclaimer, the term of this patent is extended or adjusted under 35 U.S.C. 154(b) by 830 days.

(21) Appl. No.: 10/472,838

(22) PCT Filed: Nov. 20, 2001

(86) PCT No.: PCT/US01/43229
§ 371 (c)(1), (2), (4) Date: Aug. 24, 2004

(87) PCT Pub. No.: WO02/41776
PCT Pub. Date: May 30, 2002

(65) Prior Publication Data
US 2004/0267111 A1 Dec. 30, 2004

(51) Int. Cl.
*A61B 5/055* (2006.01)
(52) U.S. Cl. .......................... 600/411; 600/439; 324/309
(58) Field of Classification Search .................. 324/307, 324/309; 600/411, 413, 427, 437, 439
See application file for complete search history.

(56) References Cited

U.S. PATENT DOCUMENTS

| | | | |
|---|---|---|---|
| 4,543,959 A | 10/1985 | Sepponen | |
| 4,739,766 A | 4/1988 | Riederer | |
| 5,032,793 A * | 7/1991 | Yamamoto et al. | 324/309 |
| 5,042,485 A * | 8/1991 | Sano et al. | 600/484 |
| 5,146,924 A | 9/1992 | Sepponen | |
| 5,524,626 A * | 6/1996 | Liu | 600/442 |
| 5,800,354 A * | 9/1998 | Hofland et al. | 600/410 |
| 5,899,861 A * | 5/1999 | Friemel et al. | 600/443 |
| 5,938,600 A * | 8/1999 | Van Vaals et al. | 600/411 |
| 6,246,898 B1 * | 6/2001 | Vesely et al. | 600/424 |
| 6,501,981 B1 * | 12/2002 | Schweikard et al. | 600/427 |
| 6,557,558 B1 * | 5/2003 | Tajima et al. | 128/897 |
| 6,937,883 B2 * | 8/2005 | Prince | 600/411 |

* cited by examiner

Primary Examiner — Brian Casler
Assistant Examiner — Jonathan G Cwern
(74) Attorney, Agent, or Firm — Cooper & Dunham, LLP

(57) ABSTRACT

A process and system acquiring both ultrasound and MRI data from a patient in an MRI scanner and using one to automatically guide or improve the other. The ultrasound data can track the motion of an organ such as a cardiac artery or the diaphragm and the resulting motion information can automatically guide MRI data acquisition to keep the imaging volume at the organ or interest, or can be used to accept or reject MRI data in the process of forming an MRI image, based on whether the organ of interest was within an acceptable range of positions. Conversely, the MRI unit can guide the ultrasound data acquisition so it is properly timed or otherwise controlled in accordance with MRI data acquisition.

10 Claims, 12 Drawing Sheets

MRI/ULTRASOUND SCANNING

ULTRASOUND IMAGE OF HEART
IN DEFINED COORDINATE SYSTEM     A.

COMPUTER-DETECT EDGE OF HEART
WALL WHERE CORONARY ARTERY LOCATED     B.

PROVIDE MRI PULSE SEQUENCE CONTROL PROGRAM     C.
WITH INFORMATION ON POSITION OF
HEART WALL (AND CORONARY ARTERY)

ALTER PULSE SEQUENCE
PER POSITION INFORMATION     D.

ACQUIRE MRI SIGNAL FROM PULSE SEQUENCE
ALTERED TO IMPROVE IMAGE OF CORONARY ARTERY
(OR CHANGE POSITION OF MRI IMAGING VOLUME,
OR ACCEPT OR REJECT MRI DATA WHEN FORMING MRI IMAGE,     E.
OR CHANGE PHASE OF MRI, OR OTHERWISE USE POSITION
INFORMATION TO IMPROVE MRI IMAGE)

PULSE SEQUENCE CONTROL PROGRAM READY
TO RECEIVE ADDITIONAL CHANGES IN
PULSE SEQUENCE FROM REPETITION     F.
OF STEPS A-E

REPEAT STEPS A-E AS NEEDED

FIG. 1

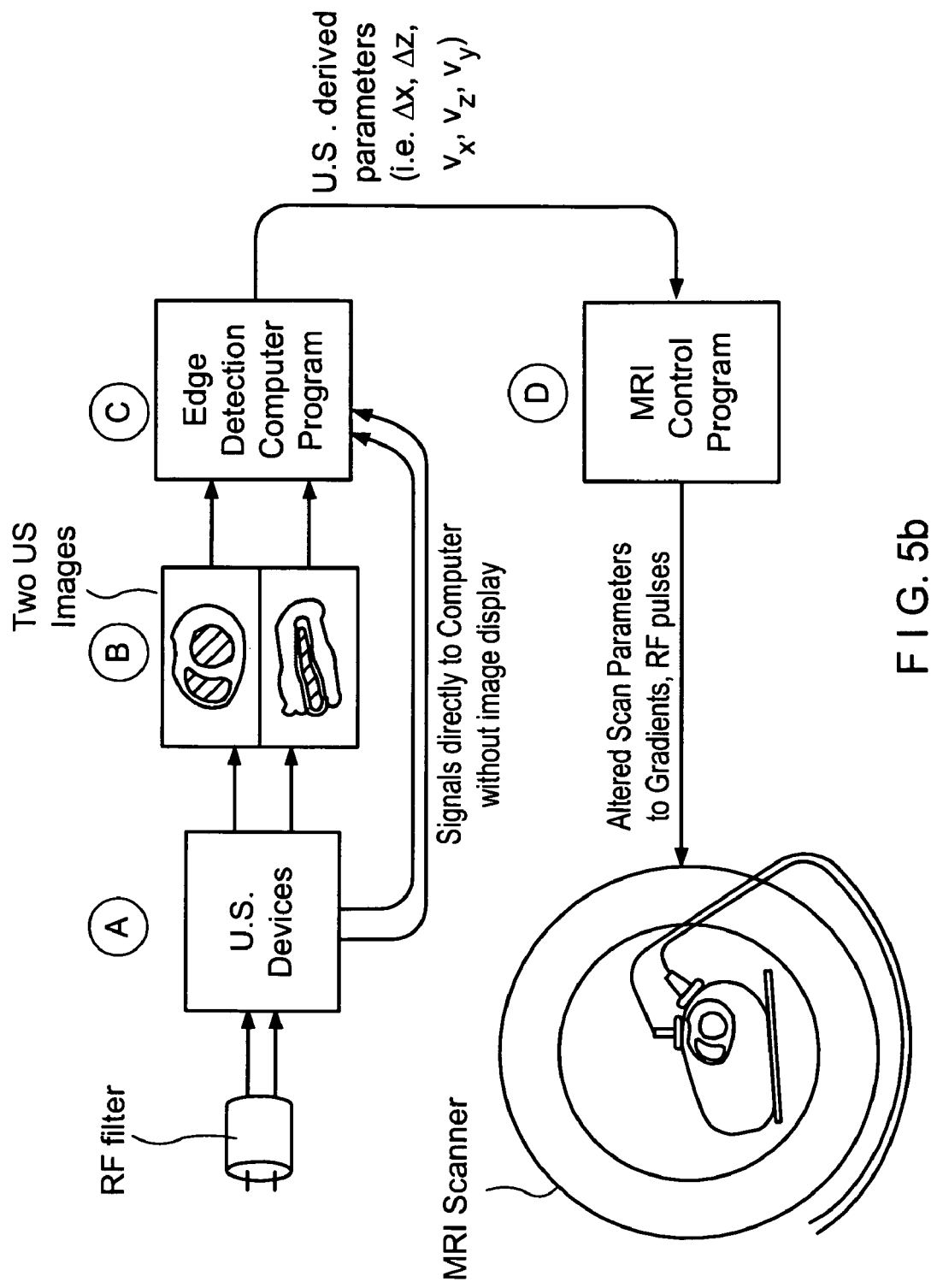
F I G. 5b

Probes directly positioned onto body will move with motion (i.e., breaking). Their position is tracked by light position monitors which update reference frame of probe in computer

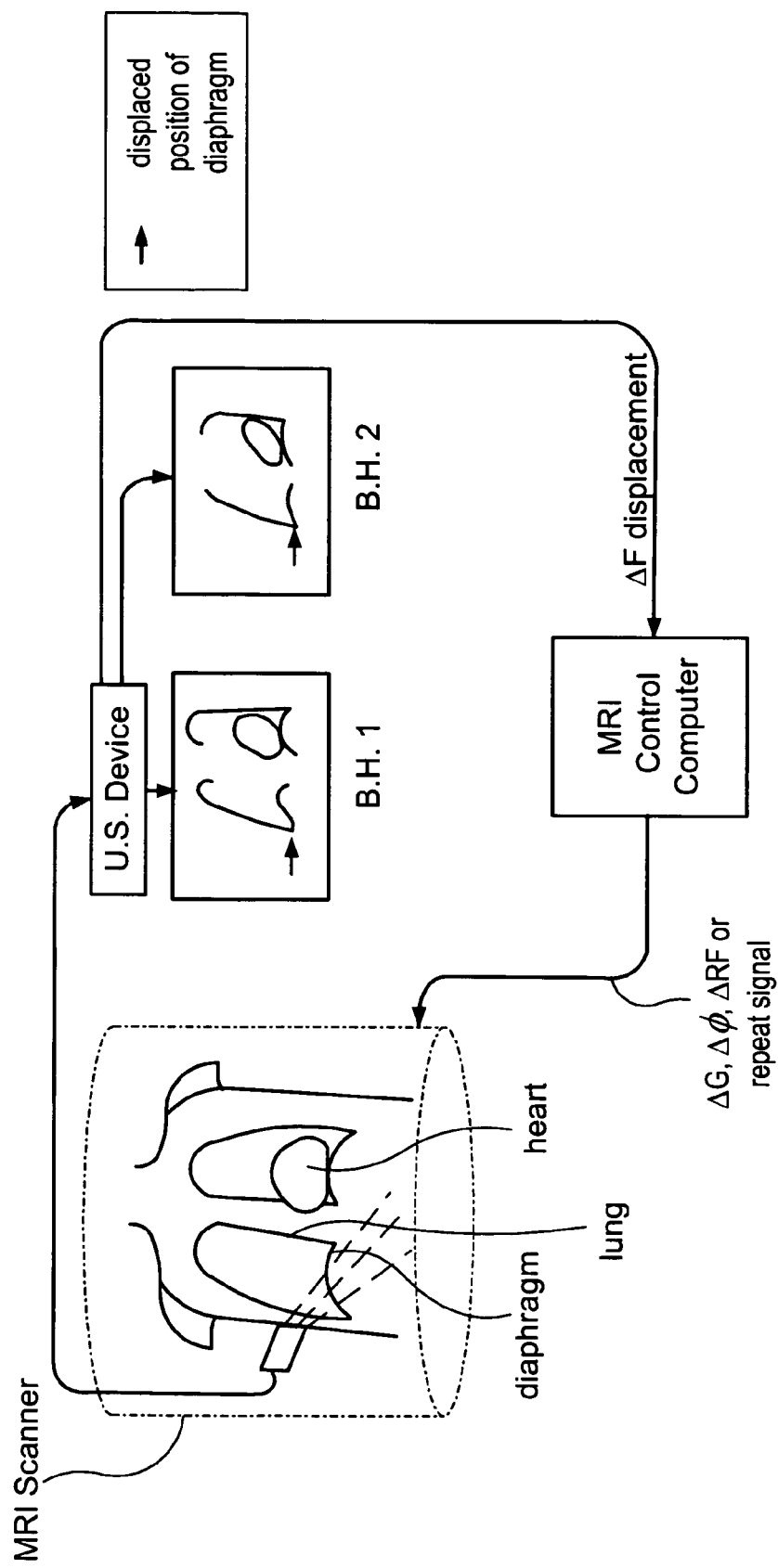
F I G. 10

ULTRASOUND WITHIN MRI SCANNERS FOR GUIDANCE OF MRI PULSE SEQUENCES

REFERENCE TO RELATED APPLICATIONS

This patent application claims the benefit of provisional application Ser. Nos. 60/252,944, 60/252,945, 60/252,950 and 60/252,953, all filed on Nov. 24, 2000, and hereby incorporates the contents of said provisional applications into this patent specification.

FIELD

This patent specification is in the field of MRI measurements and imaging and more specifically relates to using ultrasound to improve MRI measurement and imaging and, in some cases, using MRI to improve ultrasound measurements and imaging.

BACKGROUND

In MRI investigation of body, heart and chest, MRI data acquisition is limited by respiratory motion of the body to breath hold periods in order to reduce image degradation due to motion. To extend imaging time, methods of navigator echo have been implemented to measure the position of the diaphragm in multiple breath hold periods. Image acquisition is shifted to a new location as determined by the measured position of the diaphragm. A single line 1D FT image is obtained perpendicular to the diaphragm to measure the location of the diaphragm during breath holding. The level of the image acquisition is shifted in space by the measured displacement from the diaphragm's position in the first breath hold period of MRI data acquisition. Organs other than the heart, kidney, liver and pancreas have also been imaged with multiple breath hold using MRI navigator echoes. Several variants of multiple-breath hold with navigators exist but have achieved limited success due to inherent errors in measurements and variations in the correlation between measured position of the diaphragm and the heart.

The movement of an organ such as the heart during an MRI scan can and typically does cause artifacts in the image. The artifacts are due mostly to non-linearities in the data set before Fourier Transformation or back-projection reconstruction of the MRI image. Generally it is not possible to know where the moving organ was located during the MRI data acquisition without some form of gating. Gating is a process in which the MRI data collection is timed to a certain temporal point with respect to a repetitive trigger of the MRI pulse sequence. EKG signals are often used to trigger MRI pulse sequences such that each MRI signal in the final data set is obtained at the same time in the cardiac cycle and the same cardiac phase. Another approach to this problem is to oversample the data without cardiac gating so that an average position is obtained for each line of k-space in MRI signal processing. This oversampling method, taken alone, may reduce artifacts, but is still limited in obtainable spatial resolution to the time averaged position of the heart. A variant of oversampling called "retrospective navigator" (RNAV) is more effective in improving the spatial resolution in the image. The RNAV method in MRI essentially acquires an additional selective line image (1D FT line image) placed on the diaphragm or more directly on the heart or other organ to be imaged. For each line of k-space data, an RNAV signal is also obtained. The two sets of data are 1D FT processed independently and the RNAV line images are evaluated. The RNAV lines show the position of the organ and if the organ is within a certain acceptable position, the time of the RNAV is stored. The k-space data acquired at the stored time are accepted. RNAV times are selected for the final k-space data set (RNAV corrected k-space), discarding k-space data that were acquired during non-acceptable displacements. FT image reconstruction of the RNAV corrected data gives an MRI image without major blurring and with increased spatial resolution. There are limitations to the accuracy of the RNAV method, especially in the correlation between a 1D image and the 3D motion of the heart. The RNAV method works poorly when there is abnormal non-periodic motion in 3D space, as occurs with people with cardiac disease and respiratory disease that is perhaps secondary the their cardiac function.

Thus, MRI imaging and MRI pulse sequences can make use of "MRI navigator echoes" (NavEcho). The NavEcho is an MRI signal that is not directly used to make the image; instead the NavEcho signal is used to obtain information on the heart, diaphragm or other body organ that is used to improve the final image of that organ. The improvement is usually by means of correcting for body motion either by prospectively modifying an MRI pulse sequence or by retrospectively rejecting signals that have moved out of some boundary region. An example is to use a single line scan through the right diaphragm as the NavEcho. The image acquisition of the heart is then only permitted when the NavEcho identifies the diaphragm as being at a certain position. The heart position is correlated to the diaphragm position and this measure of diaphragm position effectively permits signal acquisitions of the heart only at times when the heart is in the same or nearly same position. The process reduces blurring and artifacts, up to the accuracy and reproducibility in the correlation of the positions of the two organs. Because the NavEcho signal is not acquired on the heart, there is no loss of heart MRI signal.

If the NavEcho signals are positioned on the heart, the subsequent image signals would experience a shortened T1 recovery time (time between the NavEcho and the excitation of the image signal). This would directly reduce the quality and resolution of the final image, causing signal loss and artifacts. The problem of NavEcho and signal interference would be worse using a 2D rather than a 1D NavEcho such as could be achieved with a sub-second EPI image. In this case, an entire plane of the EPI image located through the heart interferes with the NavEcho signal.

Using NavEcho requires precious time during which the image signal acquisition cannot be performed. The NavEcho and the image signals are competing for acquisition time. They are not acquired simultaneously. The ADC sampling is performed typically first for the NavEcho and then for the image signal. If a 3D image of the heart were used for the NavEcho, it would take a prohibitively long amount of time, e.g., an estimated 500 milliseconds (ms) to acquire data for a 3D GRASE single shot image. It might then take another 500 ms to perform the 3D FT and to extract an edge position on the heart. This information could be used only after a delay of 1 second or so before the information is available to direct the MRI image signal acquisition. This can be entirely useless since the heart would then typically be in an entirely different phase of a different cardiac cycle. Single line (1D) NavEcho requires only a few milliseconds (ms) to acquire, and a 1D Fourier Tranform (FT) can be processed and used within less than 100 ms. This time for NavEcho acquisition and processing of its information is useful to reposition image acquisition within the same cardiac cycle, although the temporal resolution of this process is fairly low given the heart's continuous movement in 3D space. It is not surprising that the NavEcho has limited usefulness in improving coronary MRA beyond the current 3 mm$^3$ resolution. Yet a different problem with using NavEchoes is that people with diseased hearts typically do not have predictable or reproducible respiratory motion or cardiac motion and, consequently, the NavEcho methods have poor accuracy in predicting position and timing. Thus, the NavEcho works less well in the patient population for which a highly accurate NavEcho for coronary MRA is most desired.

The idea of image fusion has been proposed for functional MRI (fMRI) and magnetoencephalography (MEG) whereby information is taken from each and combined in an image display. Spatial distribution of fMRI information can give a map of where brain activation occurs but at very low temporal resolution, down to half a second temporal resolution in some experiments. The MEG instead has very high temporal resolution, less than 50 ms, but it has less well defined spatial localization. Digital image maps are often displayed in color and show information from the MEG and fMRI combined in a 'fusion image'.

It would be desirable to find a way to guide MRI imaging prospectively, retrospectively, or both, or substantially in real time, in a way that would provide real time or near real time guidance, would not interfere with the MRI signal needed for imaging the organs of interest, and would be convenient to implement and use, but no known technique existed to meet those goals well.

SUMMARY

In a preferred embodiment, ultrasound is used to guide MRI imaging in a variety of ways. Ultrasonography (US) is a technology that can obtain cine 2D images of the heart at a frame rate of over 20-30 frames per second. The US signal is essentially based on a sound wave energy, not electromagnetic wave energy, and is not received by the radiowave tuned receiver coils of an MRI scanner. It has been discovered that US can be used to make 2D cine-images of the heart within an MRI scanner while a person is undergoing an MRI scan. A useful MRI signal can be acquired while an US transducer is positioned on the body, in the magnet, and even while the US image is being made, without interference between the US and MRI signals and without either affecting the other in an undesirable manner.

The 2D US images are interpreted by computer algorithms rapidly to determine the position of, e.g., the heart. The US information on the heart position is directly translated into computer control parameters of the MRI pulse sequence to guide or otherwise affect the next acquired MRI signal. For example, the angle and displacement of position, and also possibly the velocity of displacement of a heart wall, is measured in consecutive US frames. These US derived parameters are either translated into MRI parameters, or sent into the MRI control program where they are translated into their corresponding MRI parameters of RF pulse frequency offsets and gradient amplitudes in the selective excitations, phase shifts and/or other parameters to cause changes in the MRI pulse sequence. With these updated parameters, the new position of the heart or of a specific region of interest in the heart is translated into an angulation and displacement of the subsequently acquired MRI image volume. The US information can be updated every fraction of a cardiac cycle, e.g., every 40 ms, and can be used in the MRI signal acquisition for effectively moving the image volume to the new positions of the heart or to extrapolate in time where the heart will be located some period of time, e.g., 50 ms later, at the time of the MRI signal acquisition. This in effect makes MR imaging track the position of the heart using a priori information from US images.

Various predictive algorithms can be used to extrapolate or predict the position of the heart so as to effectively maintain the coronary artery, or some other part of the heart or of some other moving organ, in the same position with respect to the MR image volume. The reference frame of the MR image volume is determined from the coordinates obtained from the US data, and no longer held constant in position on the magnetic gradients. The above described acquired final data set of MR data is then 3D FT processed to create an MR angiogram of the coronary artery, or an image of some other organ, at higher spatial resolution and with greater accuracy since motion artifacts caused by the stationary image acquisition are removed or at least significantly reduced by the US tracking and guiding process. More image data is acquired in a given time since less data needs to be rejected. Therefore, there is a net increase in signal, the dependent SNR and image resolution. There are less or no artifacts due to changes in heart or other organ position during the MRI acquisition because the US guidance repositions the image volume to the new position of the heart or other organ being imaged by MR.

The above description is just one possible example of improving MRI images by using US data obtained in the magnet during an MRI procedure or while scanning is being performed. Another approach is to use US images to determine when cardiac motion exceeds a set limit on wall motion or displacement, then to stop the MRI acquisition until the heart again moves into the acceptable positional range at which time there is continuation of signal acquisition.

The plane of the US image is determined by the angle, location and possible movement of the US transducer system placed near or on the body. The US probes can be held in position by a mechanical arm connected to the magnet-gradient system or by clamping or otherwise securing the transducer to the body. In order to translate information accurately from US coordinates to MRI coordinates, the location and orientation of the US transducer system can be determined in the coordinate system of the magnetic gradients. This can be achieved by laser positioning of the transducer so that the exact position and orientation of the transducer system is known. As another example, MRI markers can be placed on or at the US probe, such as oil containing capsules. With an initial MRI scan to locate these markers in 3D space, the location and orientation of the probes can be defined in the MRI coordinate system. Yet another method of registering the transducer position and orientation is to use the US image and an MRI image, and varying the angle and/or position of one or the other or both until they are co-registered in the same plane.

Most of the ultrasound system, including its computer, typically can be located at a safe distance from the magnet to avoid undesirable magnetic field effect to or by the machine. The US system can be shielded to keep electronic noise generated thereby from affecting the MR receiver. The US machine can be located outside of the magnet room and outside of the RF shielding. Fiber optic cables or other suitable signal carriers can be fed through a waveguide filter through the RF shielding. Certain US transducer, commercially available, may create excessive electronic noise. The US transducer frequency can be chosen so as not to create RF frequency in the spectrum of the frequency of the MRI signal. Such precautions can ensure US generated noise is minimized and/or not received by the MRI receiver system. Hardware modification of metals in the US transducer can further reduce any possible generation of RF noise when the transducer is operating within the scanner. Thus US images can be created while the MRI receiver ADC is recording MRI data. It is also possible to gate the US transducer so as to switch it on only at times when the MRI receiver switch is turned off. This can be achieved by sending timing information on ADC sampling from the MRI pulse sequence to the US device operating the US probe. It is possible for a single computer to operate both the US and the MRI scanner and to send information between the two imaging modalities to seamlessly integrate the operation of the two different scanners.

The US images useful for MRI guidance need not be of any particular geometry or of any particular transducer geometry. A fan beam or pencil beam or a rectilinear transducer can be used. Similarly, the MRI image is not restricted to a 3D image. The MRI image can be 1D, 2D, 3D multi-slice or multi-3D slab volumes. The MRI image can be a phase or magnitude image, and there can be additional gradient pulses involved in encoding velocity in the phase image and data.

The US guided MRI can be used to image other organs, advantageously organs that move, such as the liver, kidneys or pancreas. The US image can directly track the position of these organs or it can be used to track the diaphragm or other reference organ with correlated motion. Furthermore, the US can acquire Doppler velocity measurements on vessels and this information can be used to adjust parameters in the MRI data such as the velocity encoding gradient pulses, e.g., the 'venc' of a bipolar pulse.

The US image of the heart or other organ of interest is processed to extract the MRI useful information in a time efficient manner and with necessary accuracy to yield an effective adjustment in MRI parameters. It can be desirable to first adjust the limits of a feature detection algorithm for each patient in order to achieve the above. Given the real-time or cine US imaging that can detect cyclic variations in the heart or other organ, the region of interest and limits in a detection program can be set with acceptable bounds for the actual MRI data collection. For example, the US image is oriented to show the length of the anterior wall of the left ventricle and the contraction displacements of the wall are seen as ventricle displacements of the entire wall. An edge detection algorithm can look at a limited segment of the wall for decreased computation time, or use the average position of the wall for improved SNR and decreased computation time. Several different parameters can be used simultaneously with different weightings. The parameters can be changed at different expected times in the cardiac cycle, so that different levels of decision making can be incorporated into the algorithm, such as using a new MRI position in the diastolic phase or rejecting data when displacements exceed a certain range in systolic phase. Similarly, the algorithm can be reversed in effect to obtain only a systolic phase for MRI data acquisition.

The US detection can involve one transducer or multiple transducers. The US data can be of any form, including 1D, 2D or 3D images and any of the several known US modes. It is possible to use only the raw US source data, or partially processed US data, for the MRI parameter changes, without forming a conventional US image.

The US images and probes can have known positions and/or orientations in the MRI system coordinates through different means. A gel or water bag can be used between the US transducer and the body, in acoustic contact with each, as an acoustic window on the body and also to isolate the motion of the body from the probe. The US transducer can be in a known fixed position and/or orientation in the magnet using mechanical rods to secure the transducer to a stationary object. A US transducer can be directly attached to the body and its motion can be tracked in real time using a laser tracking device, a mechanical string(s) device which measures the length of a string or strings between the transducer and a point or points on a coordinate axis direction, or some other localization system can be used, such as commercially available systems that have a moving part on the US transducer communicating via another US signals with a fixed part secured to the magnet or another object. It is desirable to eliminate sources of electronic noise from the transducer tracking or positioning devices within the magnet or even near the magnet which could lead to image artifacts.

While the application to imaging the heart and its coronary arteries is important and useful, the technology can be applied to almost any other part of the body that moves due to causes such as respiratory or cardiac cycles or for any other reason. The US arrangement can image the heart or other organs in a continuous movie frame way that can be referred to as real time imaging. The US image or data is processed in a computer to produce time varying parameters of displacement, angulation or distortions or velocity or accelerations in motion. These US-based parameters are used directly in the MRI control computer program, or they are transformed into MRI specific parameters to modify the pulse sequence, the timing of the pulse sequence, or the selection of data to be used in k-space. The US parameters can also be stored and used to modify the phase, or amplitude or to perform modification or replacement of k-space data, after the data is acquired. When the MRI pulse sequence is altered to eliminate motion dependent changes in the k-space data, the FT image has improved spatial resolution with decreased blurring and elimination of ghost artifacts. The continuous US guiding method applied throughout the MR imaging can be used to permit imaging during respiration and during a larger fraction of the cardiac cycle. Not only will the US guiding give improved co-registration in data taken at different time points, but it will also permit utilization of a larger fraction of MRI or MRA data per total imaging time, or less rejection of data. Also, the US guiding will permit a longer acquisition time in which additional data is acquired for higher spatial resolution in the image or angiogram. It is also possible to coordinate the timing between the MRI ADC sampling and the acquisition of the US data in order to prevent US machine generated noise during the ADC time sample window to prevent potential image artifacts. It is also possible to modify the US transducer switch to eliminate noise so that the US images can be acquired continuously and simultaneously during the MRI data acquisition. Because there is no undesirable coupling or interaction between the NMR relation parameters and the radiowave signal with the sound wave transmissions and reflections, both US and MRI imaging can be performed in the same locations at the same time without undesirably affecting either the US or MRI signals. The US can produce 1D to 3D spatial information in a cine acquisition to be used for MRI guidance. The US data can be analyzed in a separate computer processor then ported into the MRI control computer, or the US processing and MRI control program can be within the same computer for faster utilization of US data and decreased delay time in the guidance system.

The entire guidance system can be reversed in pathway so that the MRI is guiding the US imaging or US measurements. In this system, a parameter of displacement, velocity, or acceleration is measured in a rapidly acquired 1D or 2D MRI image which can be repeated in a continuous cine MRI imaging scheme. The MRI information is fed into spatial coordinates, as one example, which are used to modify the position and/or orientation of the US transducer. Also, the MRI image can be used to detect signal intensity changes due to passage of a bolus of contrast agents. The MRI can be used to detect changes in the intensity of signals for an organ due to contrast agents. These detected signal changes can be used to trigger, adjust or reposition the US imaging system. The known timing between MRI signal changes and US signal changes, in itself, can be used to simultaneously modify image acquisition from the two different imaging measurements.

BRIEF DESCRIPTION OF THE DRAWING

FIG. 1 is a flow chart illustrating the use of cine ultrasound (US) imaging combined with MR angiography of coronary arteries.

FIG. 5b illustrates utilization and processing of US information obtained with two probes as shown in 5a, where two US recording machines are used for guiding MRI imaging, and where the US machines/devices can be placed within the scanner room if RF filtering is not needed or if RF filtering can be accomplished by other means such as an enclosed copper box around the US machines.

FIG. 10 illustrates US guidance of an MRI scanner during multiple breath holding periods.

DETAILED DESCRIPTION

FIG. 1 illustrates a process using an ultrasound (US) system of the type that is commonly used for ultrasound imaging of internal organs such as the heart but is modified so it can be used in an MRI environment. For example, any part of the US system that can generate radio frequency (RF) interference with the MRI system is suitably shielded electrically to prevent undesirable RF emissions, and any part of the US system that could be undesirably affected by the MRI's magnetic field is made of non-magnetic materials and/or is suitably shielded magnetically.

The US system is used as is conventional with such systems to form US images of the heart at a position and orientation in a defined coordinate system that matches that of the MRI system. Using known edge detection algorithms and, if needed, a designation by an operator of a point or line on an US image displayed on a monitor, a suitably programmed computer processes the US images to detect the position of a relevant portion of the heart essentially in real time. For example, the instantaneous position of a particular coronary artery might be of interest in a given case, and this is what the computer tracks through the real time US images. In other cases, the position of a point or area on the heart wall may be of interest, and this is what is tracked through the US images. Positional information derived from tracking through the US images is provided to the MRI system, for example to serve in making relevant changes in the MRI pulse sequence that is used, in order to make sure that the MRI system acquires MRI data from a volume that includes the tracked portion of the heart, despite motion of that portion relative to the MRI magnet and coils. Stated differently, the MRI parameters are changed essentially in real time such that the portion of the heart that is of interest in the given case and the MRI coils involved in the collection of MRI data appear to be fixed relative to each other despite the heart motion. The flow chart of FIG. 1 illustrates steps in this process in an appropriate sequence, showing that the position data from an US image derived in step A is used to alter an MRI pulse sequence accordingly, and after step F another US image is used for more changes in the MRI pulse sequence to take into account the newly US-imaged position of the heart portion of interest.

The position information obtained through the US measurements or imaging in step C in FIG. 1 can be used for one or more of: (1) changing the position of the MR imaging volume so it includes the organ portion of interest despite positional changes of that organ portion relative to the MR magnet; (2) rejection MR signals if heart contraction occurs and is detected through the US system; (3) rejecting MRI data if the organ portion of interest has moved outside a desirable range in position; and (4) changing the phase of the MRI signal.

Figure 2:
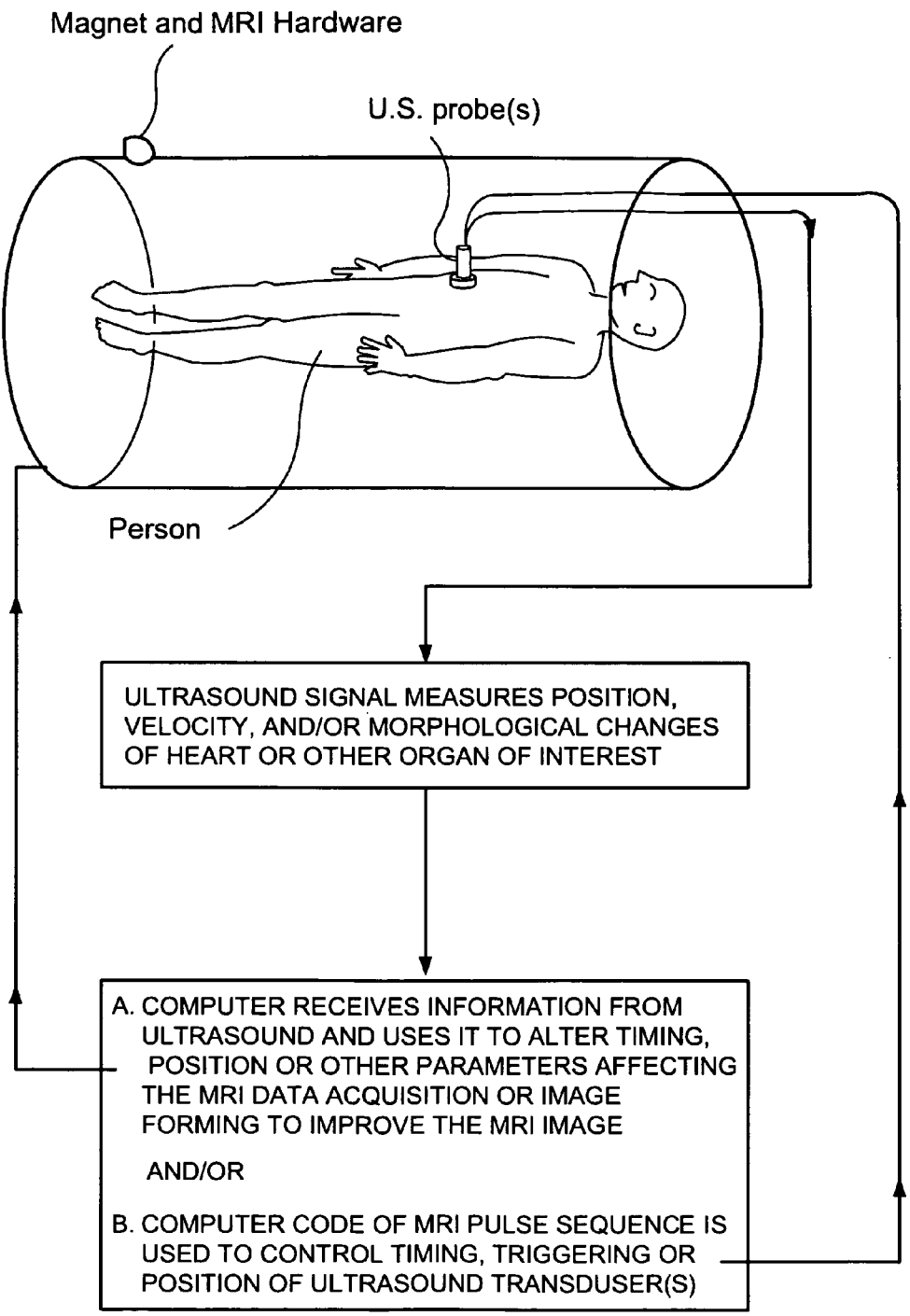
FIG. 2 illustrates an ultrasound probe (transducer) placed on a person within a magnet during MRI scanning and US scanning. The US signal is fed to computers that modify and improve the MRI imaging process.

In FIG. 2, an US probe that can comprise one or more US transducers is acoustically coupled with the body of a person in an MRI scanner. The US probe measures parameters such as the position, orientation, velocity and/or morphological changes in an organ of interest such as the heart of some other organ, using known US methods and edge designation and detection methods. Information related to the parameters measured with the US probe in real time is delivered at unit A to a computer that processes it to make it useful for altering MRI parameters in a way to essentially remove the effect of motion of the heart or other organ of interest on the MRI image. In response to this information regarding changes in MRI parameters, unit A sends appropriate MRI control parameters to the MRI system to effectively maintain the imaging volume at the moving organ of interest. In addition, MRI parameters and/or MRI data can be used at unit B to control the US probe and/or US system, for example to generate an US image at a time matching an MRI pulse sequence of some other MRI event or parameter.

Figure 3:
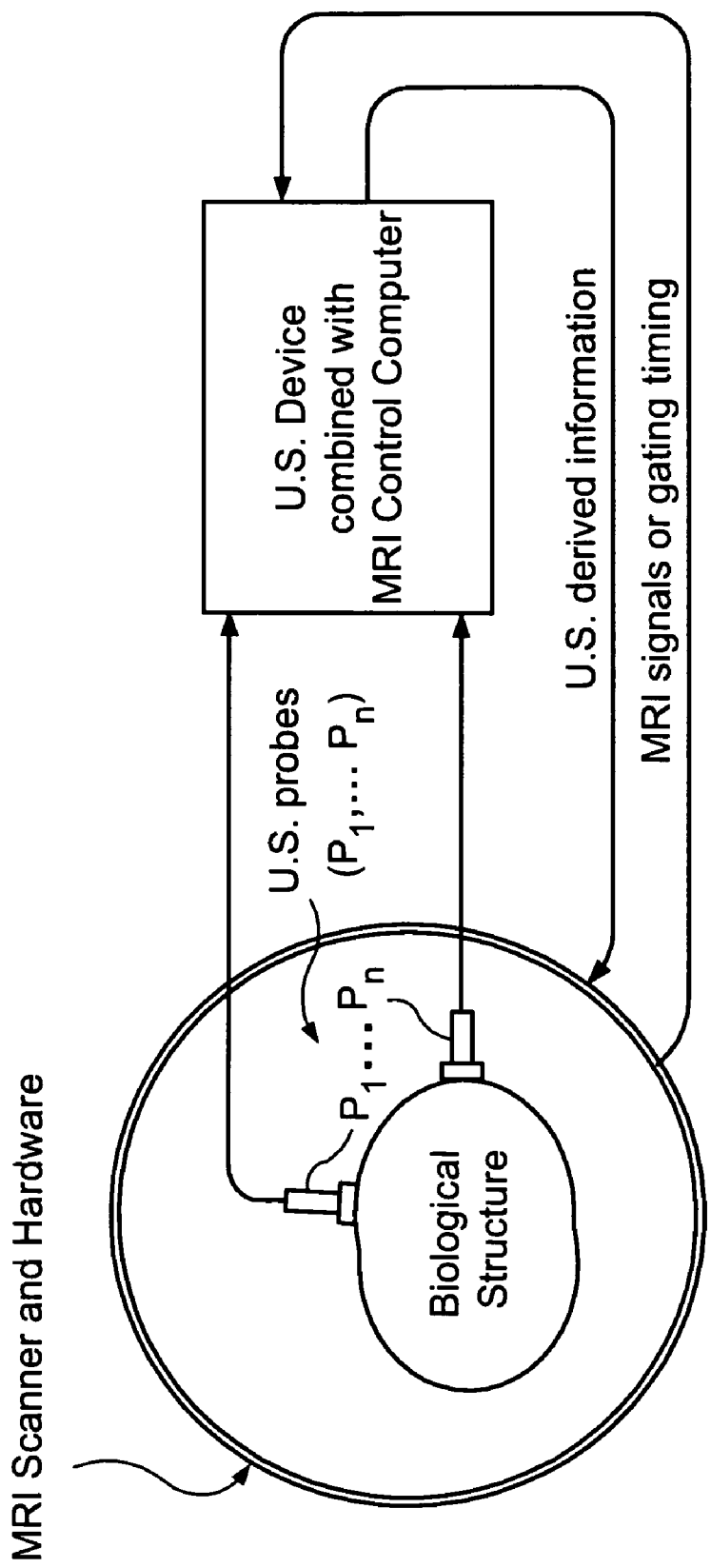
FIG. 3 illustrates MRI signals or gating timing altering the MRI signal and the US imaging.

In FIG. 3, a number of US probes P1 through Pn are acoustically coupled with a biological structure (e.g., a patient) in an MRI scanner and provide US information to a US data processing device that is coupled with or integrated with an MRI control computer. This device/computer responds to the US information from the probes to control the MRI scanner, and the MRI scanner in turn provides MRI data acquisition signals and/or gating timing to the same device/ computer for processing into MRI images and/or control purposes.

Figure 4:
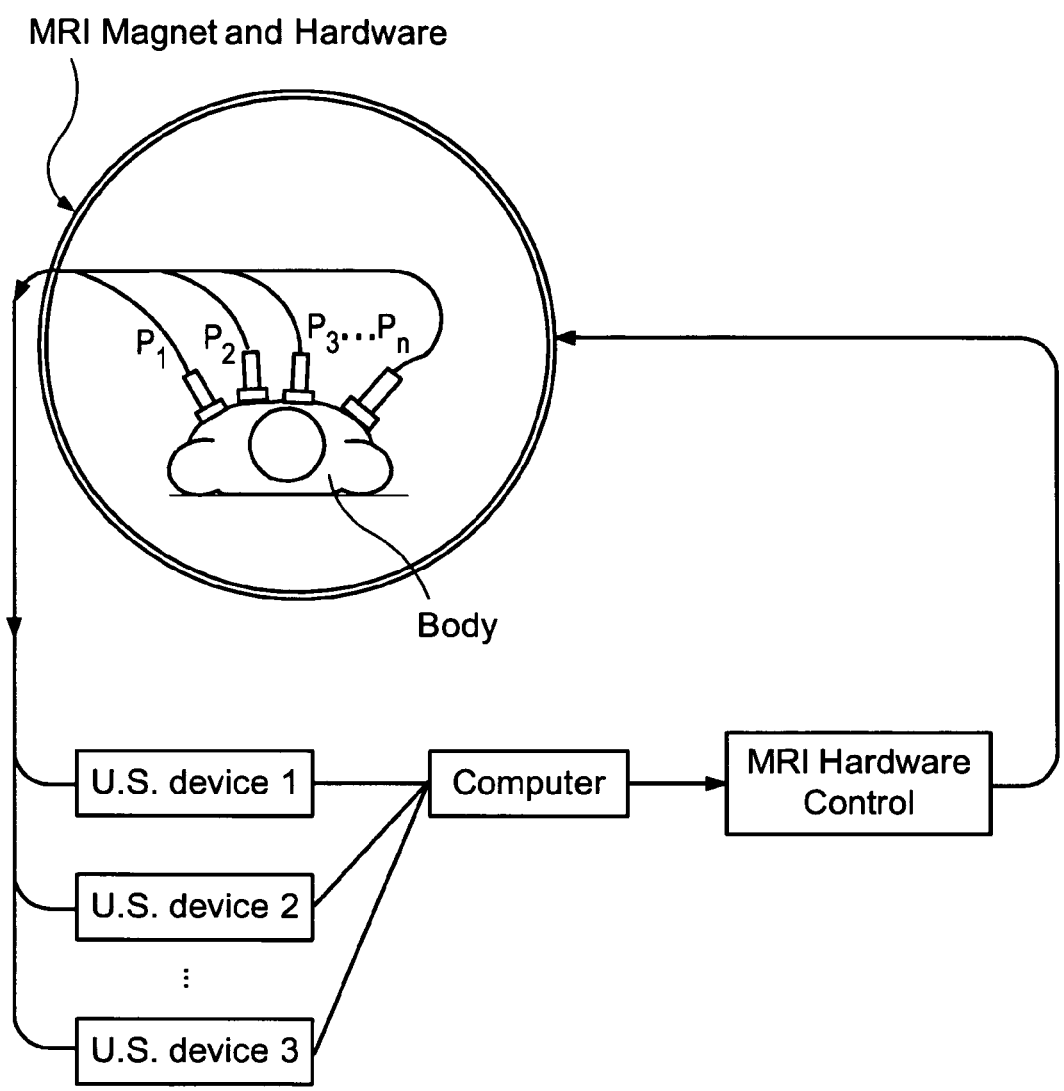
FIG. 4 illustrates a cross section of an MRI scanner using N number of US probes.

In FIG. 4, a number of US probes P1 through Pn are acoustically coupled with a body in an MRI scanner and each is coupled in two way communication with a respective US device to receive controls therefrom and to provide US data from the body thereto. The US devices can be known devices that control US transducers and process US data for US imaging or other purposes, and they in turn provide information based on the input thereto from the US probes to a computer that converts it to information for controlling MRI parameters. This information is supplied to an MRI hardware control that in turn supplies control signals to the MRI scanner to control its operation such that the active MRI imaging volume tracks the motion of the organ of interest essentially in real time.

Figure 5A:
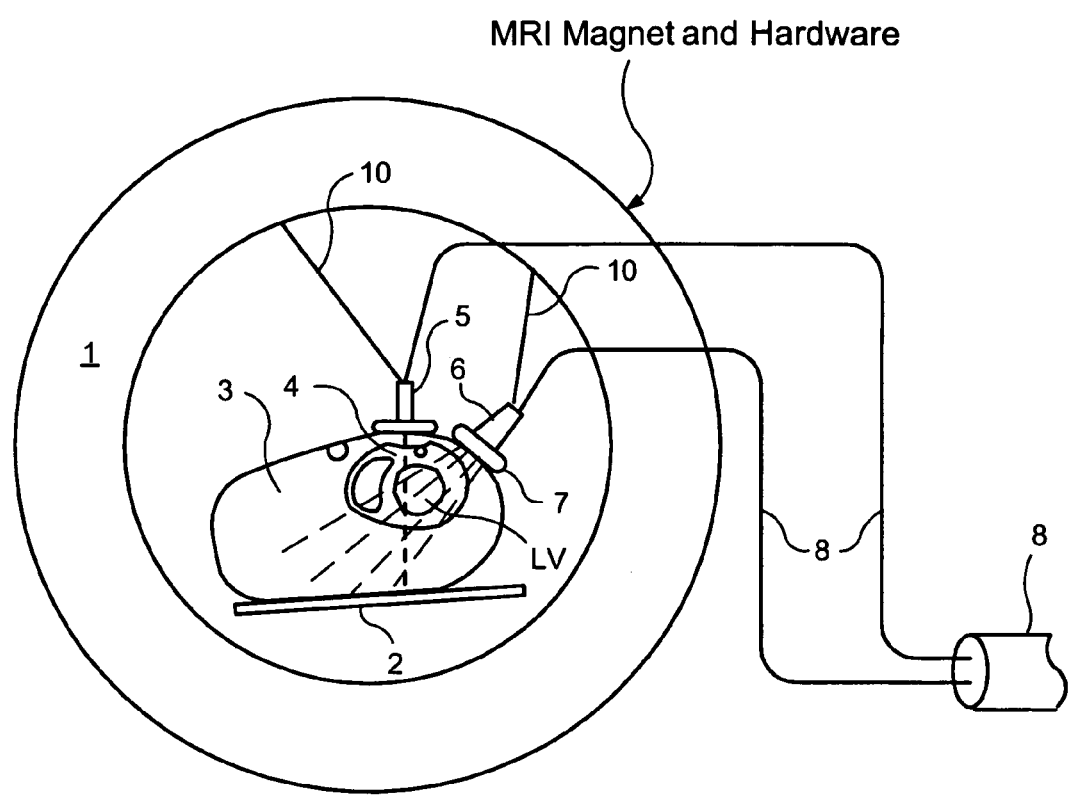
FIG. 5a illustrates a cross section of an MRI scanner using two US probes placed on interfaces that decouple body motion from the probes, with the probes placed to give two images at an angle of the same region of the heart's left ventricle (LV), for motion information in three dimensions in real-time.

In FIG. 5a, an MRI scanner 1 illustrated in cross-section has a patient table 2 supporting a person 3 whose heart 4 is being imaged with an US probes 5 and 6 that can emit fan beams of US energy in direction perpendicular to each other or at some other angle to each other. A spacer such as a soft gell bag can acoustically couple the US probes to the person. Fiber optic cables 8 can connect the probes to the outside to deliver information from and to the probes, and power can be supplied to the probes through suitably shielded connections. An RF filter 9 can be used to reduce RF interference with the MRI scanner. Mechanical arms 10 can couple the probes to the MRI scanner to follow the motion and orientation of the probes relative to the scanner, or some other system, such as an acoustical or optical tracking system, can be used to provide information regarding the current position and orientation of the probes. This position and orientation information is used to ensure that the beams of US energy and the MRI volume of interest match in space so that the US information can be used to guide the MRI data acquisition such that it acquires data from the same portion of the same organ despite relative motion between the magnet and the organ.

In FIG. 5b, which connects to the illustration of FIG. 5a through the same RF filter, as illustrated, US devices A process the US data from probes 5 and 6 and provide US image information to create and display a respective image from each probe at a display device B and/or to provide signals directly to an edge detection computer program or device C. Information regarding the current position of an organ of interest derived from the US information by program or device C, such as displacements of the organ of interest in space and velocities of such displacements, is supplied to MRI control programs or devices D that in response generate altered scan parameters such as gradient coil controls and RF pulse controls that ensure that the MRI imaging volume tracks the moving organ of interest. The US derived parameters provided by program or device C can include parameters describing displacement of the organ of interest (e.g., $\Delta x. \Delta y, \Delta z$), velocity information regarding movement of the organ of interest (e.g., $V_x, V_y, V_z$), and/or position information regarding the organ of interest.

Figure 6:
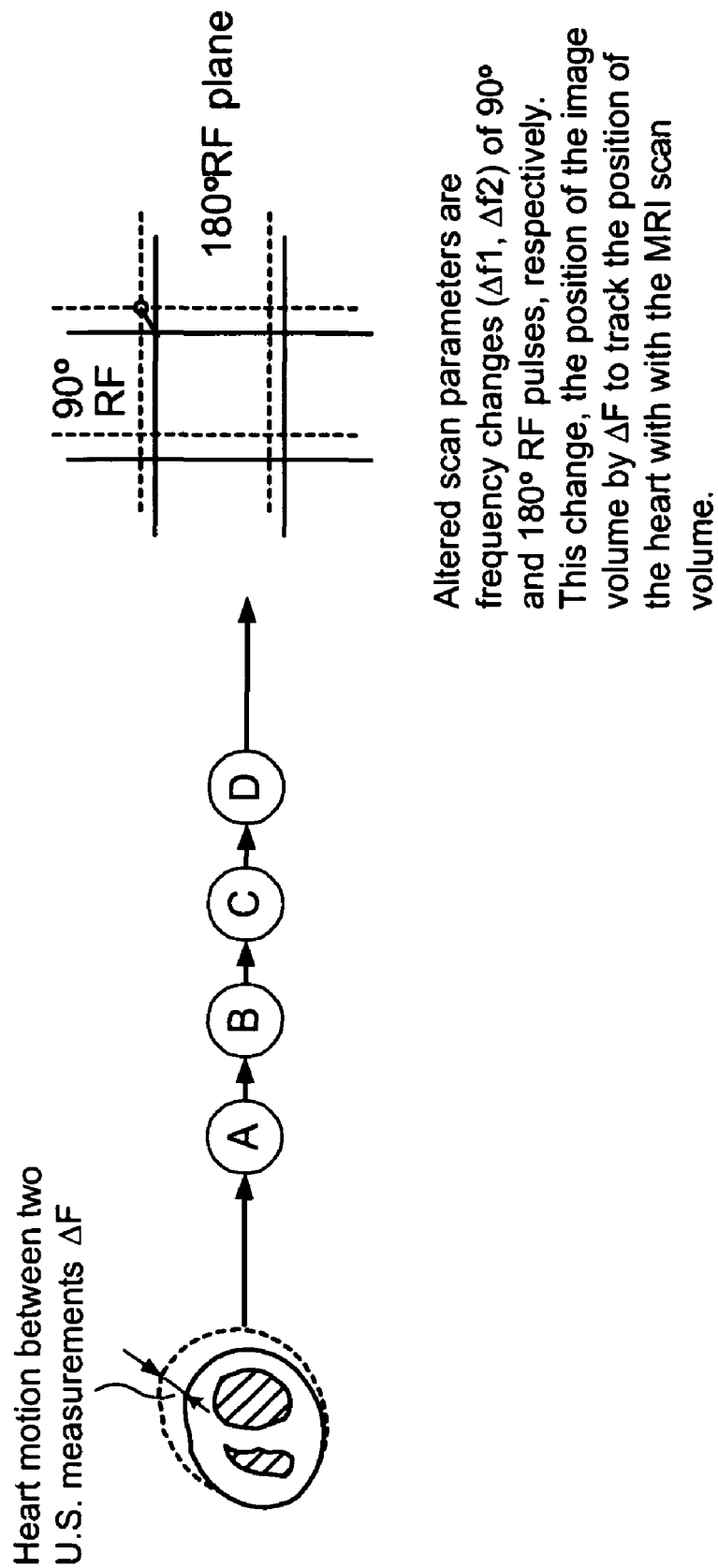
FIG. 6 illustrates an example of how two consecutive cine frames of US images can be used with only a single transducer in the system of FIGS. 5a and/or 5b to measure a displacement of the heart (delta r and dashed circle) and to cause a matching displacement in the MRI image volume.

In FIG. 6, the heart motion of a patient between two US measurement is designated by the vector $\Delta r$ and the corresponding altered MRI scan parameters are illustrated at the right hand side as frequency changes $\Delta f_1$ and delta $\Delta f_2$ for the 90° and 180° RF pulses of an MRI pulse sequence. These frequency changes change the position in space of the MRI imaging volume by the same vector $\Delta r$ to track the position of the heart with the MRI scan volume. The letters A through D designate successive US images, where the heard displacement $\Delta r$ is the displacement from one of these images to the next. The displacement of an MR the imaging volume of interest is illustrated as the change from the solid lines to the dash lines at upper right in FIG. 6.

Figure 7:
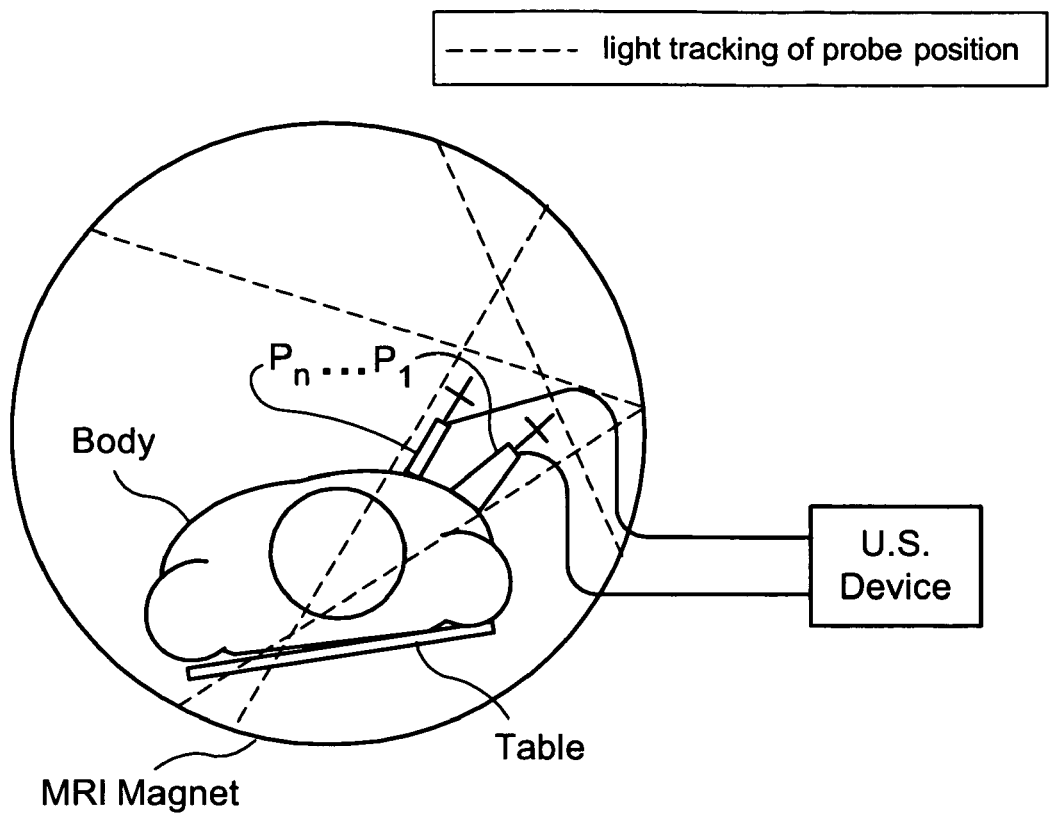
FIG. 7 illustrates US probes (transducers) placed in direct contact with a body, where the probes' positions and orientations are known in real time from mechanical transducers of probe position or by laser interfaces that measure the probe position and orientation.

FIG. 7 illustrates an MRI system in which US probes P1 through Pn are tracked with laser beams from emitters secured to the MRI scanner so that the positions and orientations of the US probes can be determined in real time relative to the MRI scanner as the probes may move in space, for example if they are directly coupled with a patient and breathing motion moves the probes relative to the MRI scanner. The US probe positions are tracked with laser position monitors which update the reference frames of the probes in a computer in the illustrated US device to which the US probes are connected.

Figure 8:
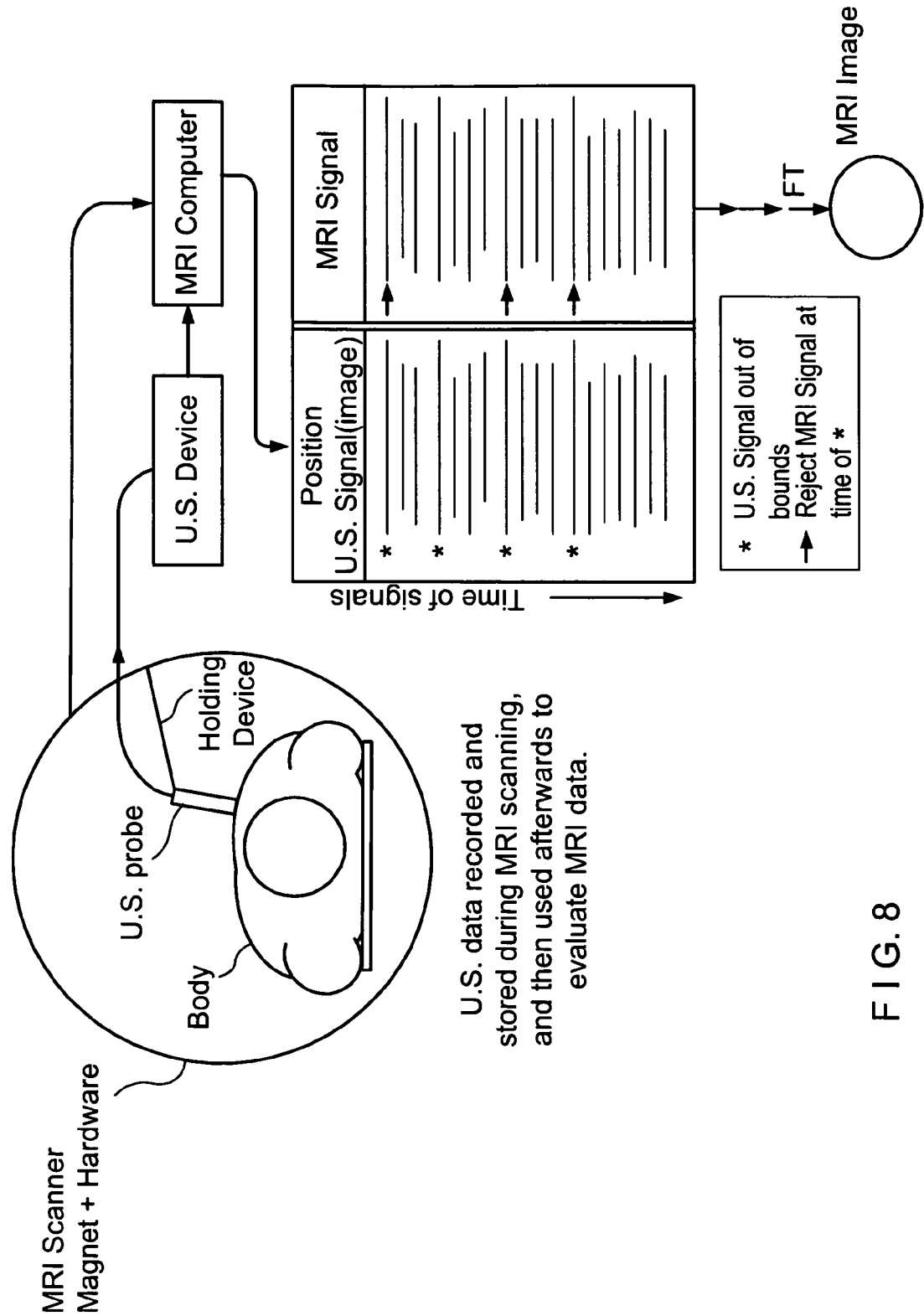
FIG. 8 illustrates recording of US data during MRI data acquisition in a process in which the US data is used to determine how the MRI data should be used in MRI image reconstruction.

In FIG. 8, US data and MRI data are recorded during MRI data acquisition and then decisions are made based on the US data to accept or reject MRI data for MRI image reconstruction. The accepted MRI data are used in further processing for image reconstruction. As illustrated, US and MR data of a patient body are acquired concurrently, with one or more US probes whose position relative to the MRI magnet and hardware is tracked via a probe holding device. The US data is initially processed at an US device and then delivered to the MRI computer, which also receives the MR data from the same patient. Both the US data and the MRI data are stored, keeping track of temporal correspondence therebetween. The US signal that is stored can be one or both of US images taken at respective times or other US measurements that relate to positions of the relevant patient organ at different times. If a selected range of acceptable positions of the body organ of interest relative to the MR magnet are preset, the US signal can be processed to mark US signals acquired when the body organ is outside the expected positional range. In FIG. 8, these US signals are marked with the symbol "*" and correspond in time to respective MRI signals. Those MRI signals can be disregarded when using FT or some other method to form an MR image from the stored MRI data.

Figure 9:
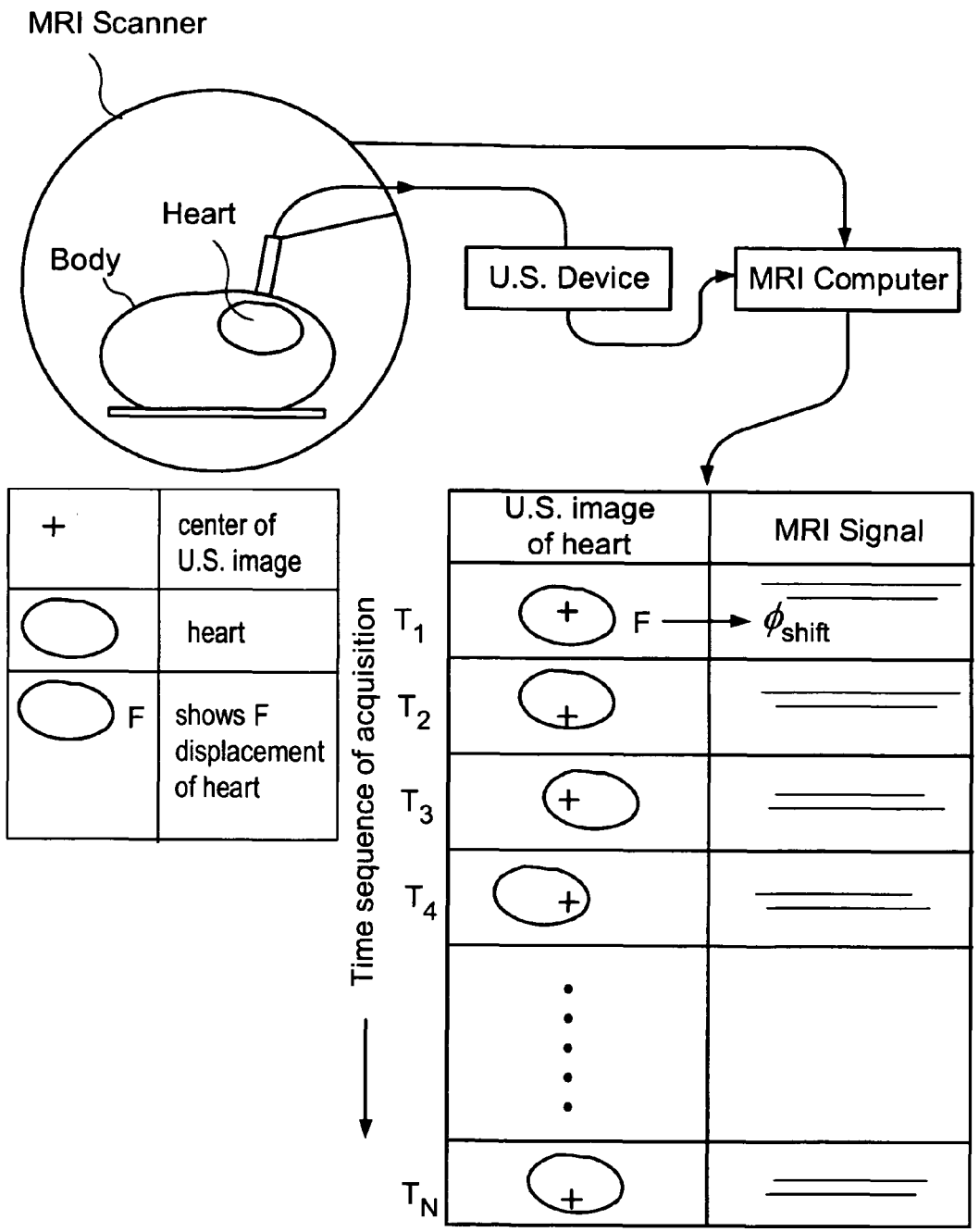
FIG. 9 illustrates recording of US data during MRI data acquisition used in another way to determine how to reconstruct an MRI image.

In FIG. 9, US and MRI data from a body (a patient) also are acquired and recorded, preferably concurrently, using an MRI scanner and one or more US probes as earlier discussed. The US data is evaluated in the illustrated US device and/or MRI computer for a displacement vector $\Delta r$, which in turn is used to modify the phase and/or amplitude of the MRI data acquired at or near the time of a corresponding US image or set of US data, using the illustrated MRI computer. The modified MRI data is used to reconstruct an MRI image. As illustrated, if the heart is the organ of interest, US images of the heart are obtained in time intervals $T_1, T_2, T_3, \ldots, T_n$ and corresponding MRI signals are acquired in the same time intervals. The US data can be used to image the heart in each of the data acquisition time intervals. If the center of each US image is identified with the marker "+" and the distance from this marker to a selected portion of the heart is measured as the displacement vector $\Delta r$, a phase shift and/or an amplitude modulation of the time-related MRI data can be carried out, and the so-shifted or modified MRI data can be used to reconstruct one or more MRI images using known reconstruction algorithms.

In FIG. 10, US data is used to guide an MRI scanner during multiple breath holding periods of k-space data acquisition. In this example, the position of the diaphragm is measured in the US image in each breath holding interval. The displacement vector $\Delta r$ representing displacement of the diaphragm between breath holding periods is used to alter parameters in the MRI control computer, which in turn alter the location of other features of subsequent MRI signals. As illustrated in this example, a patient is in an MRI magnet and one or more US probes measure the location of a selected part of the patient's diaphragm with respect to a reference fixed relative to the magnet. The US data is delivered to the illustrated US device, which produces an US image for each breath holding interval during which MRI data is acquired. Two such breath-hold images are illustrated—B.H. 1 and B.H. 2. As illustrated by the respective arrows in each US image, the patient's diaphragm is at a different positions, displaced by a displacement vector $\Delta r$ from one image to the other. The $\Delta r$ displacement information is delivered to the illustrated MRI control computer, which calculates and implements corresponding corrections $\Delta G$, $\Delta \phi$, and $\Delta RF$ in the magnetic gradients, phase and radio frequency pulses such that the MR imaging volume is at the correct position in space in the magnet to image the organ of interest in each breath holding period, or to repeat the MRI signal.

Figure 11:
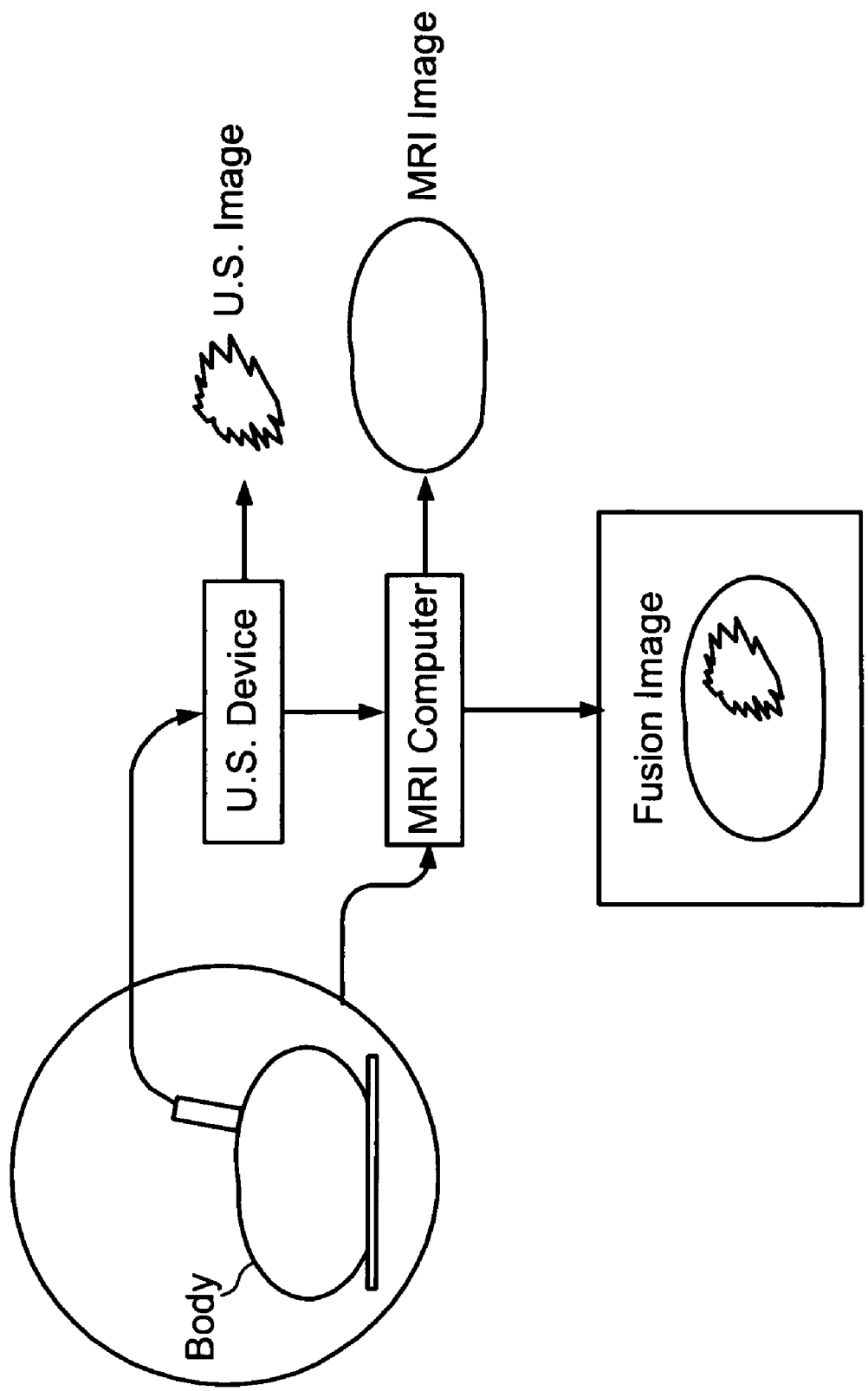
FIG. 11 illustrates concurrent acquisition of US and MRI data and a fusion thereof into a composite display.

In FIG. 11, US and MRI data are concurrently acquired. Resulting US and MRI images are fused into a composite image. As illustrated, a body is in an MRI scanner, on a suitable patient table, and one or more US probes are used to derive information for one or more US images while the MRI scanner is used to derive data for one of more MR images. The illustrated US device produces the desired image(s) while the illustrated MRI computer produces the desired MR image(s). The two types of images are fused (combined) into a single displayed image, in a display device provided with toggling capability so that the user has the choice of viewing the combined image or either of the MR and US images.

While specific examples have been illustrated above, it should be clear that many more examples will be apparent to those skilled in the art than utilize the disclosed approaches and principles and that features of one or more of the examples discussed above can be combined with features of others of those examples, and that many currently known or developed in the future processes and equipment can be used in carrying out the invention defined by the appended claims as they may be revised and clarified in prosecution of this patent application.

The invention claimed is:

1. A process of acquiring ultrasound data and magnetic resonance imaging (MRI) data of a patient in an MRI scanner such that a magnetic resonance (MR) imaging volume moves relative to the MRI scanner, under guidance from said ultrasound data, to track movement of an organ of the patient that moves relative to the MRI scanner to a plurality of different positions relative to the MRI scanner, comprising:

acquiring ultrasound data indicative of a changing position of a body organ of the patient while the organ is moving relative to the MRI scanner;

acquiring MRI data from an MR imaging volume in the patient substantially concurrently with the acquisition of the ultrasound data;

computer-processing the ultrasound data to generate guidance information causing said MR imaging volume to move relative to the MRI scanner to track the changing position of said body organ such that the MR imaging volume and said moving organ undergo matching movement with respect to the MRI scanner during said MRI data acquisition;

and computer-processing the MRI data to generate images of at least said body organ with inherent correction for motion artifacts due to said movement of the organ relative to the MRI scanner.

2. A process as in claim 1 in which said acquiring of ultrasound data comprises using at least one ultrasound transducer acoustically coupled with the patient.

3. A process as in claim 2 in which said acquiring of ultrasound data comprises using a plurality of ultrasound transducer assemblies spaced from each other along the patient and acoustically coupled to the patient to transmit ultrasound energy along beam paths at an angle to each other.

4. A process as in claim 2 in which the acquiring of ultrasound data comprises forming ultrasound images of patient anatomy.

5. A process as in claim 4 in which said forming of ultrasound images comprises forming said ultrasound images at a rate exceeding 10 images per second.

6. A process as in claim 4 including using edge detection processing to identify and track motion in space of said moving patient organ at times related to said acquiring said MRI data.

7. A process as in claim 4 in which said acquiring of said MRI data includes forming an MR image.

8. A process as in claim 7 including selectively displaying said ultrasound and MR images.

9. A process as in claim 8 including displaying a fused image related to a combination of said ultrasound and MR images.

10. A process as in claim 4 comprising using said ultrasound data to alter, during said acquisition of said MRI data, at least one of a magnetic gradient amplitude, a magnetic gradient phase, and a radio frequency pulse used in said acquisition of said MRI data.

* * * * *